US009737088B2

(12) United States Patent
Endo et al.

(10) Patent No.: US 9,737,088 B2
(45) Date of Patent: Aug. 22, 2017

(54) EMULSIFIED FOOD PRODUCT COMPOSITION (71) Applicant: OTSUKA PHARMACEUTICAL FACTORY, INC., Naruto-shi, Tokushima (JP)

(72) Inventors: Naoyuki Endo, Tokushima (JP); Kazuya Mizukai, Tokushima (JP)

(73) Assignee: OTSUKA PHARMACEUTICAL FACTORY, INC., Naruto-shi, Tokushima (JP)

( * ) Notice: Subject to any disclaimer, the term of this patent is extended or adjusted under 35 U.S.C. 154(b) by 88 days.

(21) Appl. No.: 14/385,962

(22) PCT Filed: Mar. 8, 2013

(86) PCT No.: PCT/JP2013/056422
§ 371 (c)(1),
(2) Date: Sep. 17, 2014

(87) PCT Pub. No.: WO2013/146181
PCT Pub. Date: Oct. 3, 2013

(65) Prior Publication Data
US 2015/0045453 A1 Feb. 12, 2015

(30) Foreign Application Priority Data

Mar. 30, 2012 (JP) ................................. 2012-079923

(51) Int. Cl.
A61K 9/107 (2006.01)
A23L 1/29 (2006.01)
(Continued)

(52) U.S. Cl.
CPC ............ *A23L 1/296* (2013.01); *A23L 29/015* (2016.08); *A23L 29/20* (2016.08); *A23L 29/231* (2016.08);
(Continued)

(58) Field of Classification Search
CPC ...................................................... A61K 9/107
See application file for complete search history.

(56) References Cited

U.S. PATENT DOCUMENTS 6,187,334 B1  2/2001  Yamagata et al.
6,254,905 B1  7/2001  Hojo et al.
(Continued)

FOREIGN PATENT DOCUMENTS

JP  2004-26844 A  1/2004
JP  2006-522202 A  9/2006
(Continued)

OTHER PUBLICATIONS

The FOOD Trial Collaboration (Lancet 2005; 365: 764-72).*
International Search Report of PCT/JP2013/056422, dated May 14, 2013. [PCT/ISA/210].

*Primary Examiner* — Benjamin Packard
(74) *Attorney, Agent, or Firm* — Sughrue Mion, PLLC (57) ABSTRACT The purpose of the present invention is to provide an emulsified food product composition having good fluidity and emulsification stability, even when subjected to heat sterilization treatment, with which gastro-esophageal reflux can be prevented by gelling upon entering the stomach. By adding a gelling agent for gelling in the acidic region, at least one emulsion stabilizer selected from the group consisting of gum arabic and gum ghatti, and a divalent metal salt to the emulsified food product composition comprising a lipid, it is possible to realize the property of gelling upon entering the stomach and obtain good fluidity and emulsification stability, even if a heat sterilization treatment is used.

17 Claims, 1 Drawing Sheet (51) Int. Cl.
*A61K 47/36* (2006.01)
*A23L 29/00* (2016.01)
*A23L 29/20* (2016.01)
*A23L 29/231* (2016.01)
*A23L 29/25* (2016.01)
*A23L 33/00* (2016.01)
*A23L 35/00* (2016.01)

(52) U.S. Cl.
CPC ............... *A23L 29/25* (2016.08); *A23L 33/40* (2016.08); *A23L 35/10* (2016.08); *A61K 9/107* (2013.01); *A61K 47/36* (2013.01); *A23V 2002/00* (2013.01)

(56) References Cited

U.S. PATENT DOCUMENTS

| | | | |
|---|---|---|---|
| 6,365,218 B1 * | 4/2002 | Borschel | ............... A23L 1/0541 426/573 |
| 2004/0197381 A1 | 10/2004 | Kanie | |
| 2005/0124805 A1 | 6/2005 | Al-Assaf et al. | |
| 2007/0031566 A1 | 2/2007 | Sasaki et al. | |
| 2009/0137689 A1 | 5/2009 | Al-Assaf et al. | |

FOREIGN PATENT DOCUMENTS

| | | | |
|---|---|---|---|
| JP | 2008-301723 A | | 12/2008 |
| JP | 2011-147444 A | | 8/2011 |
| WO | WO9842210 A1 | * | 8/1998 |
| WO | 98/42210 A1 | | 10/1998 |
| WO | 00/13529 A1 | | 3/2000 |
| WO | 2005/026213 A1 | | 3/2005 |
| WO | 2012/081725 A1 | | 6/2012 |

* cited by examiner

Example 1

Example 2

Comparative Example 1

Comparative Example 2

Comparative Example 3

Comparative Example 4

Comparative Example 5

EMULSIFIED FOOD PRODUCT COMPOSITION

TECHNICAL FIELD

The present invention relates to an emulsified food composition which has good fluidity and emulsification stability even when subjected to a heat sterilization treatment, and which gels upon entering into the stomach, whereby gastroesophageal reflux can be prevented.

BACKGROUND ART

Patients with brain disorder, such as cerebral apoplexy, and elderly people often have reduced swallowing function and suffer from dysphagia, in which at the time of ingesting a food, the food accidentally flows into the trachea or lung. As a method for feeding to such a dysphagic patient, a tube feeding method, in which a liquid food is administered directly into the stomach through a tube, is known. In the tube feeding method, it is important to suppress gastroesophageal reflux, which is the flow of the liquid food administered into the stomach back to the esophagus.

Conventionally, as a method for suppressing gastroesophageal reflux, a method in which a semisolid liquid food prepared by incorporating a pre-thickened thickener is administered is known (see, e.g., Patent Document 1). However, semisolid liquid foods are disadvantageous in that administration into the stomach through a tube is difficult to be made. Then, as a technique of compensating with such a disadvantage of semisolid liquid foods, a method in which a solution containing a thickener is administered through a tube before and after the tube administration of a liquid food, thereby causing the gelation of the liquid food injected into the stomach to suppress gastroesophageal reflux, has been reported (see, e.g., Patent Document 2). However, according to the technique of Patent Document 2, the administration of the solution containing a thickener is necessary in addition to the administration of liquid food, and thus there is an increased burden on the care worker. The technique also has a problem in that if, by any change, the administration of the solution containing a thickener is forgotten, gastroesophageal reflux cannot be suppressed.

Then, in recent years, as a liquid food that is fluid when ingested or administered through a tube, but turns into a semisolid upon arrival in the stomach, an emulsified food composition containing a protein, a lipid, a carbohydrate, and a thickener has been proposed (see, e.g., Patent Document 3). However, the emulsified food composition described in Patent Document 3 is disadvantageous in that when it is subjected to heat sterilization, etc., gelation occurs, resulting in loss of fluidity, and also aggregates are formed or layer separation occurs, making it impossible to maintain an good emulsified state. A food composition that cannot be heat-sterilized is also difficult to distribute or store at normal temperature. Therefore, the emulsified food composition described in Patent Document 3 has a problem in practical use that has not yet been solved.

Against this background, there has a demand for the development of an emulsified food composition which has good fluidity and emulsification stability even when subjected to a heat sterilization treatment, and which also gels upon entering into the stomach, whereby gastroesophageal reflux can be prevented.

PRIOR ART DOCUMENTS

Patent Documents

Patent Document 1: JP-A-2004-26844
Patent Document 2: WO 2000/013529, pamphlet
Patent Document 3: JP-A-2011-147444

SUMMARY OF THE INVENTION

Problems to be Solved by the Invention

An object of the prevent invention is to provide an emulsified food composition which has good fluidity and emulsification stability even when subjected to a heat sterilization treatment, and which gels upon entering into the stomach, whereby gastroesophageal reflux can be prevented.

Solutions to the Problems

The present inventor have conducted extensive research to solve the problems mentioned above. As a result, they have found that when an emulsified food composition containing a lipid has incorporated therein a thickener that gels in an acidic region, as well as at least one emulsion stabilizer selected from the group consisting of gum arabic and gum ghatti and a divalent metal salt, such that an emulsified food composition has the property of gelling upon entering into the stomach, and also can achieve good fluidity and emulsification stability even when subjected to a heat sterilization treatment, and thus it is suitable for use as a liquid food for preventing gastroesophageal reflux, especially as a liquid food for dysphagic patients. As a result of further research based on the above findings, the present invention has been accomplished.

That is, the present invention has the following modes.

Item 1. An emulsified food composition, containing (A) a lipid, (B) a thickener that gels in an acidic region, (C) at least one emulsion stabilizer selected from the group consisting of gum arabic and gum ghatti, and (D) a divalent metal salt.

Item 2. The emulsified food composition according to item 1, having a pH of 5.5 or more and less than 9.

Item 3. The emulsified food composition according to item 1, further containing at least one member selected from the group consisting of proteins and carbohydrates.

Item 4. The emulsified food composition according to item 1, wherein the thickener that gels in the acidic region (B) is at least one member selected from the group consisting of pectin, alginic acid, a salt of alginic acid, and gellan gum.

Item 5. The emulsified food composition according to item 1, wherein the thickener that gels in the acidic region (B) is low methoxyl pectin.

Item 6. The emulsified food composition according to item 1, wherein the divalent metal salt (D) is an insoluble salt that releases a divalent metal ion in an acidic region.

Item 7. The emulsified food composition according to item 1, wherein the divalent metal salt (D) is a phosphate of a divalent metal.

Item 8. The emulsified food composition according to item 1, wherein the lipid (A) is in an amount of 0.1 to 100 g/L, the thickener that gels in an acidic region (B) is in an amount of 1 to 70 g/L, the at least one emulsion stabilizer selected from the group consisting of gum arabic and gum ghatti (C) is in an amount of 0.5 to 70 g/L, and the divalent metal salt (D) is in an amount of 0.1 to 10 g/L.

Item 9. The emulsified food composition according to item 1, having a viscosity of 2 to 100 mPa·s at 25° C.

Item 10. The emulsified food composition according to item 1, used to feed a nutrient to a dysphagic patient.

Item 11. Use of an emulsified food composition for producing an enteral nutrient for dysphagic patients, the emulsified food composition containing (A) a lipid, (B) a thickener that gels in an acidic region, (C) at least one emulsion stabilizer selected from the group consisting of gum arabic and gum ghatti, and (D) a divalent metal salt.

Item 12. A method for feeding a nutrient to a dysphagic patient, including the step of administering an emulsified food composition to an dysphagic patient through a tube, the emulsified food composition containing (A) a lipid, (B) a thickener that gels in an acidic region, (C) at least one emulsion stabilizer selected from the group consisting of gum arabic and gum ghatti, and (D) a divalent metal salt.

Effects of the Invention

The emulsified food composition of the present invention has excellent fluidity and emulsification stability and also gels upon entering into the stomach. Accordingly, it can be easily administered through a tube, and further gastroesophageal reflux can be also prevented.

In addition, the emulsified food composition of the present invention can maintain excellent fluidity and emulsification stability even when subjected to a heat sterilization treatment. Therefore, the emulsified food composition of the present invention can be subjected to heat sterilization such as pressure/heat sterilization or ultrahigh temperature sterilization (UHT), allowing for distribution or long-term storage at normal temperature. Accordingly, there is a great advantage not only in terms of distribution but also in terms of quality control.

EMBODIMENTS OF THE INVENTION

The emulsified food composition of the present invention is characterized by containing a lipid (hereinafter sometimes referred to as "component (A)"), a thickener that gels in an acidic region (hereinafter sometimes referred to as "component (B)"), at least one emulsion stabilizer selected from the group consisting of gum arabic and gum ghatti (hereinafter sometimes referred to as "component (C)"), and a divalent metal salt (hereinafter sometimes referred to as "(D) component"). Hereinafter, the emulsified composition of the present invention will be described in detail.

[Component (A)]

The emulsified composition of the present invention contains a lipid as component (A). The kind of lipid used in the present invention is not particularly limited, and examples thereof include vegetable oils such as rice oil, coconut oil, soybean oil, corn oil, rapeseed oil, palm oil, safflower oil, sunflower oil, soybean oil, olive oil, cottonseed oil, peanut oil, and cacao butter; animal oils such as fish oil, tallow, and lard; fatty acids, medium-chain fatty acid (approximately $C_{6-12}$) triglycerides, docosahexaenoic acid, eicosapentaenoic acid, and the like. The fat or oil incorporated in the emulsified food composition of the present invention may be a single kind or may be also a combination of two or more kinds.

The amount of component (A) incorporated in the emulsified food composition of the present invention is suitably determined according to the kind of component (A) used, etc., and may be, for example, 0.1 to 100 g/L, preferably 5 to 70 g/L, and still more preferably 10 to 40 g/L.

[Component (B)]

The emulsified composition of the present invention contains a thickener that gels in an acidic region as component (B). The thickener that gels in an acidic region is not particularly limited as long as it is edible and has the property that it does not gel in a neutral region but gels in an acidic region. As such a thickener, a thickener that gels in a region where the pH is about 5 or less can be mentioned, for example. Specific examples thereof include pectin, alginic acid, a salt of alginic acid, gellan gum, and carrageenan.

The pectin mentioned above is a polysaccharide obtained by acid extraction from plants such as sugar beets, sunflowers, oranges, grapefruits, limes, lemons, and apples. The pectin used in the present invention may be obtained by extraction from plants as mentioned above, etc., or may be also produced through chemical synthesis, enzymatic synthesis, microbial fermentation, etc. The pectin for use in the present invention may be either high methoxyl pectin with an esterification degree of 50% or more or low methoxyl pectin with an esterification degree of less than 50%, or may be also a mixture thereof. In terms of providing excellent fluidity and emulsification stability and also more effectively imparting the property of gelling upon entering into the stomach, low methoxyl pectin is preferable.

The alginic acid and the salt of alginic acid mentioned above are polysaccharides obtained by extraction from algae such as brown algae. The alginic acid and the salt of alginic acid used in the present invention may be obtained by extraction from algae as mentioned above, etc., or may be also produced through chemical synthesis, enzymatic synthesis, microbial fermentation, etc. Here, specific examples of salts of alginic acid include alkali metal salts such as sodium salt and potassium salt.

The gellan gum mentioned above is a polysaccharide produced by *Sphingomonas elodea*. The gellan gum used in the present invention may be obtained by the fermentation of microorganisms as mentioned above, etc., or may be also produced through chemical synthesis, enzymatic synthesis, etc.

The carrageenan mentioned above is a polysaccharide obtained by extraction from algae such as red algae. The carrageenan used in the present invention may be obtained by extraction from algae as mentioned above, etc., or may be also produced through chemical synthesis, enzymatic synthesis, etc.

These components (B) may be used alone or in combination of two or more kinds.

Among these components (B), in terms of allowing fluidity and emulsification stability to be maintained even after a heat sterilization treatment and also more effectively imparting the property of gelling upon entering into the stomach, pectin, alginic acid, a salt of alginic acid, and gellan gum are preferable; pectin is still more preferable; and low methoxyl pectin is particularly preferable.

The amount of component (B) incorporated in the emulsified food composition of the present invention is suitably determined according to the kind of component (B) used, etc., and may be, for example, 1 to 70 g/L, preferably 3 to 50 g/L, and still more preferably 5 to 30 g/L.

[Component (C)]

The emulsified food composition of the present invention contains at least one emulsion stabilizer selected from the group consisting of gum arabic and gum ghatti as component (C).

The gum arabic mentioned above is a thickener obtained by drying a secretion from the resin of *Acacia senegal* or its allied congeners (e.g., *Acacia senegal, Acacia abysinica, Acacia glaucophylla, Acacia reficiens, Acacia fistula, Acacia giraffae*, etc.). The gum arabic used in the present invention may be obtained from plants as mentioned above, or may be also produced through chemical synthesis, enzymatic synthesis, etc.

The gum ghatti mentioned above is a thickener obtained by drying a sap extracted from the trunk of a plant, such as *Anogeissus latifolia*. The gum ghatti used in the present invention may be obtained from plants as mentioned above, or may be also produced through chemical synthesis, enzymatic synthesis, etc.

In the emulsified food composition of the present invention, the component (C) may be one member selected from gum arabic and gum ghatti, or may be also a combination thereof.

Among these components (C), in terms of allowing fluidity and emulsification stability to be maintained even after a heat sterilization treatment and also yet more effectively imparting the property of gelling upon entering into the stomach, gum ghatti is preferable.

The amount of component (C) incorporated in the emulsified food composition of the present invention is suitably determined according to the kind of component (C) used, etc., and may be, for example, 0.5 to 70 g/L, and preferably 0.5 to 50 g/L.

More specifically, in the case where the component (C) is gum arabic, the amount of component (C) incorporated in the emulsified food composition of the present invention may be usually 20 to 70 g/L, preferably 30 to 60 g/L, and still more preferably 40 to 50 g/L. In addition, in the case where the component (C) is gum ghatti, the amount of component (C) incorporated in the emulsified food composition of the present invention may be usually 0.5 to 20 g/L, preferably 0.5 to 15 g/L, still more preferably 3 to 10 g/L, and particularly preferably 3 to 7.5 g/L.

[(D) Component]

The emulsified food composition of the present invention contains a divalent metal salt as component (D). When the components (A) to (D) are contained all together, this makes it possible for the emulsified composition of the present invention to have good fluidity and emulsification stability even when subjected to a heat sterilization treatment and also have the property of gelling upon entering into the stomach.

Specific examples of divalent metals forming the divalent metal salt include magnesium, calcium, and barium. Among these, magnesium and calcium are preferable.

A divalent metal ion promotes the thickening or gelation of the thickener. Therefore, it is preferable that the divalent metal salt used in the present invention is an insoluble salt that releases a divalent metal ion in an acidic region. The "insoluble salt that releases a divalent metal ion in an acidic region" herein refers to a salt that is insoluble or poorly soluble in a neutral or basic region, but dissolves in an acidic region to release a divalent metal ion. In addition, "insoluble" means that 10,000 g or more of water is required to dissolve 1 g of a sample, while "poorly soluble" means that 1,000 to 10,000 g of water is required to dissolve 1 g of a sample. When an insoluble salt that releases a divalent metal ion in an acidic region is used as component (D), this makes it possible that thickening or gelation is not promoted during distribution or storage, and, the thickening or gelation of the thickener is promoted with a decrease in pH upon entering into the stomach. Specific examples of insoluble salts that release a divalent metal ion in an acidic region include phosphates of divalent metals, such as tricalcium phosphate and trimagnesium phosphate; oxides of divalent metals, such as calcium oxide and magnesium oxide; and carbonates of divalent metals, such as calcium carbonate and magnesium carbonate. Among these, phosphates of divalent metals are preferable.

In addition, the divalent metal salt may be a chloride of a divalent metal, a sulfate of a divalent metal, a divalent metal salt of an organic acid, or the like as long as it is designed to not release a divalent metal ion in a neutral region but release a divalent metal ion at an acidic pH with stomach-soluble coating or by forming a soluble complex ion through combined use with orthophosphate, polyphosphate, or the like.

These components (D) may be used alone or in combination of two or more kinds.

Among these components (D), in terms of allowing fluidity and emulsification stability to be maintained even after a heat sterilization treatment and also more effectively imparting the property of gelling upon entering into the stomach, a phosphate of a divalent metal, an oxide of a divalent metal, and a carbonate of a divalent metal are preferable; a phosphate of a divalent metal is still more preferable, and calcium phosphate and magnesium phosphate are particularly preferable.

The amount of component (D) incorporated in the emulsified food composition of the present invention is suitably determined according to the kind of component (C) used, etc., and may be, for example, 0.1 to 10 g/L, preferably 0.5 to 7 g/L, and still more preferably 1 to 5 g/L.

[Additional Components]

In addition to the components (A) to (D), the emulsified food composition of the present invention may contain either a protein or a carbohydrate, and preferably both of them.

The protein is not particularly limited in origin. Examples thereof include proteins of plant origin, such as soybeans, wheat, peas, and rice; animal origin, such as eggs, fish and shellfish, meat, milk, and collagen, etc. In addition, these proteins may be depolymerized by enzymatic decomposition, etc. The protein incorporated in the emulsified food composition of the present invention may be a single kind or may be also a combination of two or more kinds.

In the case where a protein is incorporated in the emulsified food composition of the present invention, the amount thereof incorporated is suitably determined according to the kind of protein used, etc., and may be, for example, 5 to 100 g/L, preferably 10 to 80 g/L, and still more preferably 30 to 70 g/L.

In addition, the carbohydrate is not particularly limited in kind. Examples thereof include monosaccharides such as glucose, galactose, fructose, and xylose; disaccharides such as sucrose, lactose, and maltose; oligosaccharides such as galactosaccharide, xylooligosaccharide, soybean oligosaccharide, fructooligosaccharide, and lactosucrose; and polysaccharides such as dextrin, dietary fibers, and starch. The carbohydrate incorporated in the emulsified food composition of the present invention may be a single kind or may be also a combination of two or more kinds.

In the case where a carbohydrate is incorporated in the emulsified food composition of the present invention, the amount thereof incorporated is suitably determined according to the kind of carbohydrate used, etc., and may be, for example, 1 to 500 g/L, preferably 10 to 400 g/L, and still more preferably 100 to 300 g/L.

The emulsified food composition of the present invention is in an emulsified form and contains water. The amount of water incorporated in the emulsified food composition of the present invention is not particularly limited, and may be, for example, 500 to 990 g/L, preferably 600 to 950 g/L, and still more preferably 700 to 900 g/L.

As necessary, the emulsified food composition of the present invention may further contain emulsifiers such as lecithin, sucrose fatty acid ester, glycerin fatty acid ester, and sorbitan fatty acid ester, and additives such as pH adjusters, vitamins, minerals, sweeteners, antioxidants, preservatives, seasonings, colorants, and perfumes.

[Physical Properties of Emulsified Food Composition]

The emulsified form of the emulsified food composition of the present invention is not particularly limited, and may be an oil-in-water type or a water-in-oil type, and preferably an oil-in-water type.

In addition, in terms of maintaining good fluidity without causing gelation or thickening during distribution and storage, the pH of the emulsified food composition of the present invention may be usually 5.5 or more and less than 9, and preferably 6.0 to 8.0.

In addition, the emulsified food composition of the present invention usually has a viscosity of 2 to 100 mPa·s, preferably 3 to 70 mPa·s, and still more preferably 5 to 50 mPa·s, and thus has good fluidity. Accordingly, it can be easily administered through a gastrostomy tube or a transnasal tube. The viscosity herein is a value measured at 25° C. using a Brookfield viscometer with an L-adapter at a rotation speed of 12 rpm.

The energy density of the emulsified food composition of the present invention is not particularly limited and is suitably determined according to the purpose of use, etc. The energy density may be, for example, 0.1 to 7 kcal/g, preferably 0.3 to 5 kcal/g, and still more preferably 0.5 to 3 kcal/g.

[Production Method for Emulsified Food Composition]

The production method for the emulsified food composition of the present invention is not particularly limited, and it can be produced in the same manner as in the production of an ordinary emulsified food product. Specifically, the emulsified composition of the present invention can be produced by adding the predetermined amounts of the components (A) to (D) to water together with the additional components to be incorporated as necessary, mixing them, and emulsifying the mixture in a homogenizer. In the production method for the emulsified food composition of the present invention, the order of the addition of the components is not particularly limited. However, it is preferable that at the time of adding the component (B), the liquid mixture to which the component (B) is to be added has been adjusted to a pH range where gelation is not caused by the component (B).

In addition, it is preferable that the emulsified food composition of the present invention is subjected to a heat sterilization treatment before or after packaged in a container such as an aluminum pouch or a soft bag. Through such a heat sterilization treatment, storage stability can be improved. The temperature conditions for the heat sterilization treatment are not particularly limited, and a temperature of 110 to 150° C., preferably 120 to 145° C., can be mentioned, for example. Specific examples of heat sterilization treatments include pressure/heat sterilization, ultra-high temperature sterilization (UHT), and high-temperature short-time sterilization (HTST). Even when subjected to such a heat sterilization treatment, the emulsified composition of the present invention can suppress thickening or gelation, and the fluidity and emulsified state can be stably maintained without the formation of aggregates or the occurrence of layer separation.

[Application and Use of Emulsified Food Composition]

The emulsified food composition of the present invention can be also used as a nutraceutical food for healthy individuals. However, it has the property of having moderate fluidity until entering into the stomach and gelling upon entering into the stomach, and thus is suitable for use as a food product for those who need the prevention of gastroesophageal reflux (i.e., a food product for the prevention of gastroesophageal reflux), especially as an enteral nutrient for dysphagic patients. Further, the emulsified food composition of the present invention can gel upon entering into the stomach to adjust the transit time of food in the digestive tract, thereby preventing diarrhea. Accordingly, it is also useful as a food product for the prevention of diarrhea.

The form of ingestion or administration of the emulsified food composition of the present invention is not particularly limited. For example, when used as a nutraceutical food for healthy individuals, it can be orally ingested. When used for a dysphagic patient, it can be administered through a tube such as a gastrostomy tube (catheter) or a transnasal tube (catheter).

The amount of the emulsified food composition of the present invention to be ingested or administered is suitably determined according to its energy density and the conditions, sex, age, and the like of the person who ingests or is administered with it. For example, the amount of the emulsified food composition of the present invention to be ingested or administered each time may be about 50 to 1000 g, and preferably about 150 to 600 g, and it may be ingested or administered one to five times a day, and preferably one to three times a day.

EXAMPLES

Hereinafter, the present invention will be described in further detail with reference to examples. Incidentally, the present invention is not limited to the following embodiments.

Test Example 1

Evaluation of Emulsification Stability

Emulsified food compositions of the composition shown in Table 1 (OW-type) were prepared. Incidentally, the kinds and amounts of emulsion stabilizers incorporated are as shown in Table 2. Specifically, the components except for low methoxyl pectin were added to water and mixed in a mixer. Subsequently, the pH was adjusted (pH 7), and low methoxyl pectin was added, followed by homogenization in a high-pressure homogenizer (RANNIE, Mini-Lab, type 8.30H, manufactured by APV) (50 MP, 2 passes). One hundred (100) mL of the homogenized emulsified food composition was packaged in a pouch and subjected to a heat sterilization treatment (121° C., 10 minutes). After heat sterilization, each emulsified food composition was allowed to stand at 25° C. overnight, and the occurrence of oil layer separation was visually checked to evaluate emulsification stability. Incidentally, the evaluation of emulsification stability was performed according to the following criteria.

<Criteria for Emulsification Stability>
5: Oil layer separation or aggregate formation is not seen at all.
4: Oil layer separation and aggregate formation are slightly seen.
3: Oil layer separation and aggregate formation are apparently seen, but they can be resuspended by mixing.
2: Oil layer separation and aggregate formation are apparently seen, and they cannot be resuspended by mixing.
1: Significant oil layer separation and aggregate formation have occurred, and they cannot be resuspended by mixing.

TABLE 1

| Components | | Proportion (g/L) |
|---|---|---|
| Lipid | Rice oil ("Rice Salad Oil", TSUNO CO., LTD.) | 23 |
| Thickener | Low methoxyl pectin ("GENU Pectin", Sansho Co., Ltd.) | 12 |
| Emulsion stabilizer | See Table 2 | See Table 2 |
| Divalent metal salt | Tricalcium phosphate ("VERSACAL MP", organo foodtech corporation) | 1.7 |
| | Trimagnesium phosphate ("Trimagnesium Phosphate", Taihei Chemical Industrial Co., Ltd.) | 1.7 |
| Protein | Casein enzymatic decomposition product ("TATUA2391", Tatua Japan Company Limited) | 50 |
| Carbohydrate | Dextrin ("TK-16", Matsutani Chemical Industry Co., Ltd.) | 150 |
| pH adjuster | Sodium hydroxide ("Sodium Hydroxide", Kanto Chemical Co., Inc.) | Proper quantity (Adjust to pH 7 before adding thickener) |
| Water | Purified water | Remainder |
| | Energy density | 1000 kcal/L |

TABLE 2

| | Kind of Emulsion Stabilizer | Proportion (g/L) |
|---|---|---|
| Example 1 | Gum arabic ("Efistab AA", Colloides Naturels Japan Inc.) | 40 |
| Example 2 | Gum ghatti ("Gum Ghatti SD", San-Ei Gen F.F.I., Inc.) | 5 |
| Comparative Example 1 | Enzymatically decomposed lecithin ("Sunlecithin A-1", Taiyo Kagaku Co., Ltd.) | 7.9 |
| Comparative Example 2 | Sucrose fatty acid ester, glycerin fatty acid ester ("RYOTO CP-Y040", Mitsubishi-Kagaku Foods Corporation) | 2.2 |
| Comparative Example 3 | Glycerin fatty acid ester ("Poem DP-95RF", RIKEN VITAMIN CO., LTD.) | 2.2 |
| Comparative Example 4 | Sucrose fatty acid ester ("RYOTO Sugar Ester S570", Mitsubishi-Kagaku Foods Corporation) | 0.5 |
| | Sucrose fatty acid ester ("RYOTO Sugar Ester P1670", Mitsubishi-Kagaku Foods Corporation) | 1.1 |
| Comparative Example 5 | Organic acid monoglyceride ("Sunsoft No. 681 NU", Taiyo Kagaku Co., Ltd.) | 3.3 |

TABLE 3

| | Results of the Evaluation of Emulsification Stability |
|---|---|
| Example 1 | 5 |
| Example 2 | 5 |
| Comparative Example 1 | 1 |
| Comparative Example 2 | 1 |

Figure 1:
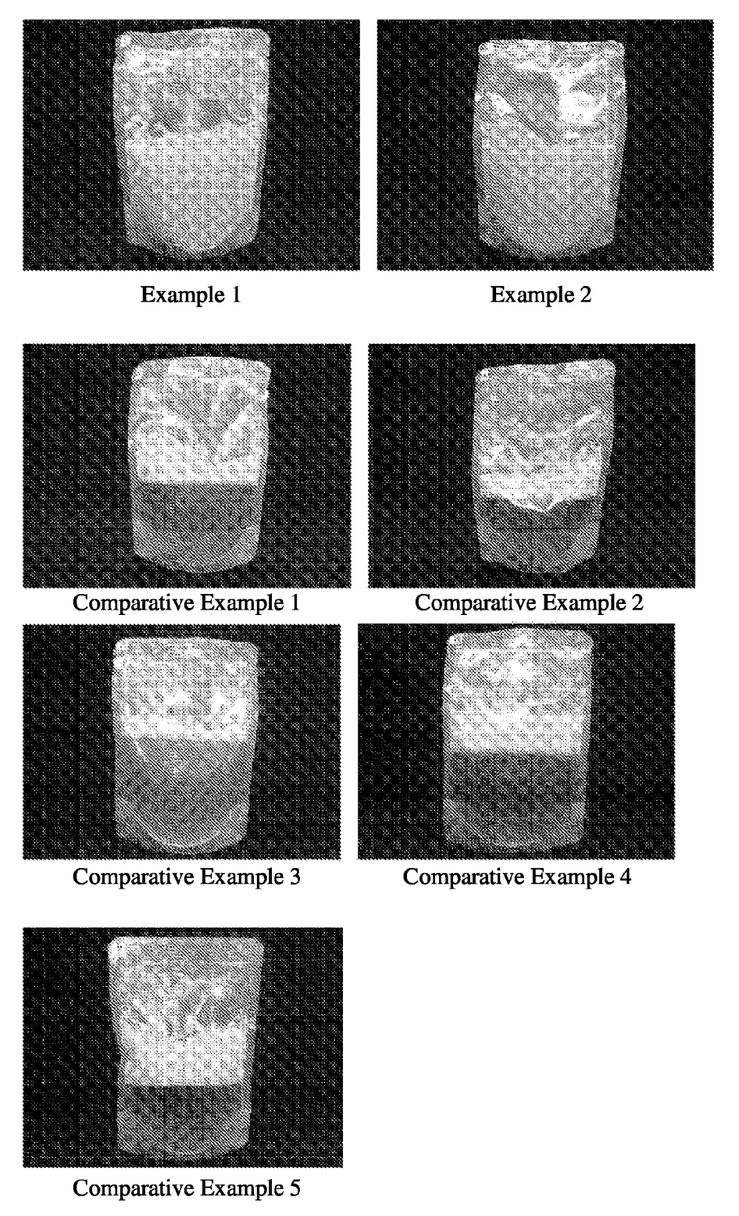
FIG. 1 shows the results of photographing the appearance of emulsified food compositions allowed to stand overnight in Test Example 1.

The obtained results are shown in Table 3. In addition, FIG. 1 shows the results of photographing the appearance of the emulsified food compositions allowed to stand overnight. As is obvious from Table 3 and FIG. 1, in the case where gum arabic or gum ghatti was used as an emulsion stabilizer, even when the composition was subjected to a heat sterilization treatment and then stored, the separation of the oil layer or the formation of aggregates was not seen at all, and a good emulsified state was maintained. In addition, in the emulsified food composition using gum arabic or gum ghatti, thickening or gelation did not occur even after allowing to stand overnight, and good fluidity was maintained. Meanwhile, in the case of using the emulsion stabilizers of Comparative Examples 1 to 5, signs of oil layer separation were seen immediately after the heat sterilization treatment. After allowing to stand overnight, the separation of the oil layer and the formation of aggregates occurred, destabilizing the emulsified state.

TABLE 3-continued

| | Results of the Evaluation of Emulsification Stability |
|---|---|
| Comparative Example 3 | 1 |
| Comparative Example 4 | 1 |
| Comparative Example 5 | 1 |

Test Example 2

Evaluation of Gelation Characteristics Upon Mixing with Artificial Gastric Juice Emulsified food compositions of the composition shown in Table 4 (OW-type) (Examples 3 and 4) were prepared.

Specifically, the components except for low methoxyl pectin were added to water and mixed in a mixer. Subsequently, the pH was adjusted (pH 7), and low methoxyl pectin was added, followed by homogenization in a high-pressure homogenizer (RANNIE, Mini-Lab, type 8.30H, manufactured by APV) (50 MP, 2 passes). One hundred (100) mL of the homogenized emulsified food composition was packaged in a pouch and subjected to a heat sterilization treatment (121° C., 10 minutes).

The heat-sterilized emulsified food composition was taken out from the pouch, and the viscosity at 25° C. was measured using a Brookfield viscometer (type RB80L, manufactured by TOKI SANGYO CO., LTD.) with an L-adapter at a rotation speed of 12 rpm. In addition, 50 ml of the emulsified composition taken out from the pouch was placed in a tall beaker (100-ml volume), and further 50 ml of artificial gastric juice produced in accordance with "6.09 Disintegration Test" of The Japanese Pharmacopoeia, 16th Edition, (pH 1.2, sodium chloride: 2.0 g/L, hydrochloric acid: 7.0 ml/L) was added. The two were mixed, and the viscosity of the obtained liquid mixture at 25° C. was measured using the above device with an M3 adapter at a rotation speed of 12 rpm.

Test Example 3

Evaluation of Influence of the Amount of Gum Arabic on Emulsification Stability

Emulsified food compositions of the composition shown in Table 6 (OW type) (Examples 5 to 9) were prepared by varying the amount of gum arabic incorporated. Specifically, the components except for low methoxyl pectin were added to water and mixed in a mixer. Subsequently, the pH was adjusted (pH 7), and low methoxyl pectin was added, followed by homogenization in a high-pressure homogenizer (RANNIE, Mini-Lab, type 8.30H, manufactured by APV) (50 MP, 2 passes). One hundred (100) mL of the homogenized emulsified food composition was packaged in a pouch and subjected to a heat sterilization treatment (121° C., 10 minutes). After heat sterilization, each emulsified food composition was allowed to stand at 25° C. overnight, and the occurrence of oil layer separation was visually checked to evaluate emulsification stability. Incidentally, the

TABLE 4

| | Components | Example 3 | Example 4 |
|---|---|---|---|
| Lipid | Rice oil ("Rice Salad Oil", TSUNO CO., LTD.) | 23 | 23 |
| Thickener | Low methoxyl pectin ("GENU Pectin", Sansho Co., Ltd.) | 12 | 12 |
| Emulsion stabilizer | Gum arabic ("Efistab AA", Colloides Naturels Japan Inc.) | 40 | — |
| | Gum ghatti ("Gum Ghatti SD", San-Ei Gen F.F.I., Inc.) | — | 5 |
| Divalent metal salt | Tricalcium phosphate ("VERSACAL MP", organo foodtech corporation) | 1.7 | 1.7 |
| | Trimagnesium phosphate ("Trimagnesium Phosphate", Taihei Chemical Industrial Co., Ltd.) | 1.7 | 1.7 |
| Protein | Casein enzymatic decomposition product ("TATUA2391", Tatua Japan Company Limited) | 50 | 50 |
| Carbohydrate | Dextrin ("TK-16", Matsutani Chemical Industry Co., Ltd.) | 150 | 150 |
| pH adjuster | Sodium hydroxide ("Sodium Hydroxide", Kanto Chemical Co., Inc.) | Proper quantity (Adjust to pH 7 before adding thickener) | Proper quantity (Adjust to pH 7 before adding thickener) |
| Water | Purified water | Remainder | Remainder |
| | Energy density | 1000 kcal/L | 1000 kcal/L |

In the table, the unit of component proportion is "g/L".

The results of the measurement of viscosity before and after mixing with the artificial gastric juice are shown in Table 5. From these results, it was confirmed that the emulsified food compositions of Examples 3 and 4 have good fluidity until it contacts with the gastric juice, and is thicken and gel upon contact with the gastric juice. From these results, it was confirmed that the emulsified food composition of the present invention gels when administered into the stomach, whereby gastroesophageal reflux can be prevented.

TABLE 5

| | Viscosity at 25° C. Immediately after Preparation (mPa · s) | Viscosity at 25° C. after Mixing with Artificial Gastric Juice (mPa · s) |
|---|---|---|
| Example 3 | 13.8 | 4400 |
| Example 4 | 11.6 | 3400 | evaluation of emulsification stability was performed in the same manner as in the above test example.

In addition, the heat-sterilized emulsified food composition was taken out from the pouch, and the viscosity at 25° C. was measured using a Brookfield viscometer (type RB80L, manufactured by TOKI SANGYO CO., LTD.) with an L-adapter at a rotation speed of 12 rpm. Incidentally, in the case where the specimen had high viscosity beyond the measurement range of the device, the rotation speed in the measurement was suitably reduced. In addition, 50 ml of the emulsified composition taken out from the pouch was placed in a tall beaker (100-ml volume), and further 50 ml of artificial gastric juice produced in accordance with "6.09 Disintegration Test" of The Japanese Pharmacopoeia, 16th Edition, (pH 1.2, sodium chloride: 2.0 g/L, hydrochloric acid: 7.0 ml/L) was added. The two were mixed, and the viscosity of the obtained liquid mixture at 25° C. was measured using the above device with an M3 adapter at a rotation speed of 12 rpm.

TABLE 6

| Components | | Proportion (g/L) |
|---|---|---|
| Lipid | Rice oil ("Rice Salad Oil", TSUNO CO., LTD.) | 23 |
| Thickener | Low methoxyl pectin ("GENU Pectin", Sansho Co., Ltd.) | 12 |
| Emulsion stabilizer | Gum arabic ("Efistab AA", Colloides Naturels Japan Inc.) | See Table 7 |
| Divalent metal salt | Tricalcium phosphate ("VERSACAL MP", organo foodtech corporation) | 1.7 |
| | Trimagnesium phosphate ("Trimagnesium Phosphate", Taihei Chemical Industrial Co., Ltd.) | 1.7 |
| Protein | Casein enzymatic decomposition product ("TATUA2391", Tatua Japan Company Limited) | 50 |
| Carbohydrate | Dextrin ("TK-16", Matsutani Chemical Industry Co., Ltd.) | 150 |
| pH adjuster | Sodium hydroxide ("Sodium Hydroxide", Kanto Chemical Co., Inc.) | Proper quantity (Adjust to pH 7 before sterilization) |
| Water | Purified water | Remainder |
| | Energy density | 1000 kcal/L |

In the table, the unit of component proportion is "g/L".

The obtained results are shown in Table 7. From these results, it was confirmed that an emulsified food composition having incorporated therein 20 to 70 g/L of gum arabic (Examples 5 to 9) has excellent emulsification stability and good fluidity before mixing with artificial gastric juice, and, after mixing with artificial gastric juice, it gels to the extent that gastroesophageal reflux can be prevented.

TABLE 7

| | Proportion of gum arabic (g/L) | Results of the Evaluation of Emulsification Stability | Viscosity at 25° C. Immediately after Preparation (mPa · s) | Viscosity at 25° C. after Mixing with Artificial Gastric Juice (mPa · s) |
|---|---|---|---|---|
| Example 5 | 20 | 3 | 12.3 | 5510 |
| Example 6 | 30 | 4 | 11.3 | 4310 |
| Example 7 | 40 | 5 | 13.8 | 4400 |
| Example 8 | 50 | 5 | 22.1 | 3760 |
| Example 9 | 70 | 5 | 51.4 | 2198 |

Test Example 4

Evaluation of Influence of the Amount of Gum Ghatti on Emulsification Stability

Emulsified food compositions of the composition shown in Table 8 (OW type) (Examples 10 to 16) were prepared by varying the amount of gum ghatti incorporated. Specifically, the components except for low methoxyl pectin were added to water and mixed in a mixer. Subsequently, the pH was adjusted (pH 7), and low methoxyl pectin was added, followed by homogenization in a high-pressure homogenizer (RANNIE, Mini-Lab, type 8.30H, manufactured by APV) (50 MP, 2 passes). One hundred (100) mL of the homogenized emulsified food composition was packaged in a pouch and subjected to a heat sterilization treatment (121° C., 10 minutes). After heat sterilization, each emulsified food composition was allowed to stand at 25° C. overnight, and the occurrence of oil layer separation was visually checked to evaluate emulsification stability. Incidentally, the evaluation of emulsification stability was performed in the same manner as in the above test example.

In addition, the heat-sterilized emulsified food composition was taken out from the pouch, and the viscosity at 25° C. was measured using a Brookfield viscometer (type RB80L, manufactured by TOKI SANGYO CO., LTD.) with an L-adapter at a rotation speed of 12 rpm. Incidentally, in the case where the specimen had high viscosity beyond the measurement range of the device, the rotation speed in the measurement was suitably reduced. In addition, 50 ml of the emulsified composition taken out from the pouch was placed in a tall beaker (100-ml volume), and further 50 ml of artificial gastric juice produced in accordance with "6.09 Disintegration Test" of The Japanese Pharmacopoeia, 16th Edition, (pH 1.2, sodium chloride: 2.0 g/L, hydrochloric acid: 7.0 ml/L) was added. The two were mixed, and the viscosity of the obtained liquid mixture at 25° C. was measured using the above device with an M3 adapter at a rotation speed of 12 rpm.

TABLE 8

| Components | | Proportion (g/L) |
|---|---|---|
| Lipid | Rice oil ("Rice Salad Oil", TSUNO CO., LTD.) | 23 |
| Thickener | Low methoxyl pectin ("GENU Pectin", Sansho Co., Ltd.) | 12 |
| Emulsion stabilizer | Gum ghatti ("Gum Ghatti SD", San-Ei Gen F.F.I., Inc.) | See Table 9 |
| Divalent metal salt | Tricalcium phosphate ("VERSACAL MP", organo foodtech corporation) | 1.7 |
| | Trimagnesium phosphate ("Trimagnesium Phosphate", Taihei Chemical Industrial Co., Ltd.) | 1.7 |
| Protein | Casein enzymatic decomposition product ("TATUA2391", Tatua Japan Company Limited) | 50 |

TABLE 8-continued

| | Components | Proportion (g/L) |
|---|---|---|
| Carbohydrate | Dextrin ("TK-16", Matsutani Chemical Industry Co., Ltd.) | 150 |
| pH adjuster | Sodium hydroxide ("Sodium Hydroxide", Kanto Chemical Co., Inc.) | Proper quantity (Adjust to pH 7 before sterilization) |
| Water | Purified water | Remainder |
| | Energy density | 1000 kcal/L |

In the table, the unit of component proportion is "g/L".

The obtained results are shown in Table 9. From these results, it was confirmed that an emulsified food composition having incorporated therein 0.5 to 20 g/L, particularly 3 to 10 g/L, of gum ghatti has excellent emulsification stability and good fluidity before mixing with artificial gastric juice, and, after mixing with artificial gastric juice, it gels to the extent that gastroesophageal reflux can be prevented.

TABLE 9

| | Proportion of gum ghatti (g/L) | Results of the Evaluation of Emulsification Stability | Viscosity at 25° C. Immediately after Preparation (mPa · s) | Viscosity at 25° C. after Mixing with Artificial Gastric Juice (mPa · s) |
|---|---|---|---|---|
| Example 10 | 0.5 | 3 | 8.9 | 4770 |
| Example 11 | 3 | 5 | 10.1 | 4020 |
| Example 12 | 5 | 5 | 11.6 | 3400 |
| Example 13 | 7.5 | 5 | 18.1 | 5040 |
| Example 14 | 10 | 5 | 41.4 | 3750 |
| Example 15 | 15 | 5 | 373.5 | 1980 |
| Example 16 | 20 | 5 | 756.0 | 1080 |

The invention claimed is:

1. An emulsified food composition, comprising
(A) a lipid,
(B) a thickener that gels in an acidic region,
(C) at least one emulsion stabilizer selected from the group consisting of gum arabic and gum ghatti, and
(D) a divalent metal salt,
wherein the divalent metal salt (D) is an insoluble salt that releases a divalent metal ion in an acidic region,
an amount of the divalent metal salt (D) is 0.1 to 10 g/L,
(i) the at least one emulsion stabilizer (C) is gum ghatti, and an amount of gum ghatti is 0.5 to 20 g/L, or (ii) the at least one emulsion stabilizer (C) is gum arabic, and an amount of gum arabic is 20 to 70 g/L, and
the emulsified food composition has a pH of 5.5 or more and less than 9.

2. The emulsified food composition according to claim 1, having a pH of 6.0 to 8.0.

3. The emulsified food composition according to claim 1, further comprising at least one member selected from the group consisting of proteins and carbohydrates.

4. The emulsified food composition according to claim 1, wherein the thickener that gels in the acidic region (B) is at least one member selected from the group consisting of pectin, alginic acid, a salt of alginic acid, and gellan gum.

5. The emulsified food composition according to claim 1, wherein the thickener that gels in the acidic region (B) is low methoxyl pectin.

6. The emulsified food composition according to claim 1, wherein the divalent metal salt (D) is a phosphate of a divalent metal.

7. The emulsified food composition according to claim 1, wherein the lipid (A) is in an amount of 0.1 to 100 g/L, and the thickener that gels in an acidic region (B) is in an amount of 1 to 70 g/L.

8. The emulsified food composition according to claim 1, having a viscosity of 2 to 100 mPa·s at 25° C.

9. A method for feeding a nutrient to a dysphagic patient, comprising the step of administering an emulsified food composition to an dysphagic patient through a tube, the emulsified food composition containing (A) a lipid, (B) a thickener that gels in an acidic region, (C) at least one emulsion stabilizer selected from the group consisting of gum arabic and gum ghatti, and (D) a divalent metal salt,
wherein the divalent metal salt (D) is an insoluble salt that releases a divalent metal ion in an acidic region,
an amount of the divalent metal salt (D) is 0.1 to 10 g/L, and
(i) the at least one emulsion stabilizer (C) is gum ghatti, and an amount of gum ghatti is 0.5 to 20 g/L, or (ii) the at least one emulsion stabilizer (C) is gum arabic, and an amount of gum arabic is 20 to 70 g/L, and
the emulsified food composition has a pH of 5.5 or more and less than 9.

10. The emulsified food composition according to claim 1, wherein the divalent metal salt (D) is at least one selected from the group consisting of tricalcium phosphate, trimagnesium phosphate, an oxide, a chloride or a sulfate of a divalent metal, and magnesium carbonate.

11. The method according to claim 9, wherein the divalent metal salt (D) is at least one selected from the group consisting of tricalcium phosphate, trimagnesium phosphate, an oxide, a chloride or a sulfate of a divalent metal, and magnesium carbonate.

12. The emulsified food composition according to claim 1, wherein the emulsified food composition is in a form of an oil-in-water type emulsion.

13. The method according to claim 9, wherein the emulsified food composition is in a form of an oil-in-water type emulsion.

14. The emulsified food composition according to claim 1, wherein the at least one emulsion stabilizer (C) is gum arabic,
an amount of gum arabic is 20 to 70 g/L, and
an amount of the divalent metal salt (D) is 0.1 to 10 g/L.

15. The emulsified food composition according to claim 1, wherein the at least one emulsion stabilizer (C) is gum ghatti,
an amount of gum ghatti is 0.5 to 20 g/L, and
an amount of the divalent metal salt (D) is 0.1 to 10 g/L.

16. The method according to claim 9, wherein the at least one emulsion stabilizer (C) is gum arabic,
an amount of gum arabic is 20 to 70 g/L, and
an amount of the divalent metal salt (D) is 0.1 to 10 g/L.

17. The method according to claim 9, wherein the at least one emulsion stabilizer (C) is gum ghatti,
   an amount of gum ghatti is 0.5 to 20 g/L, and
   an amount of the divalent metal salt (D) is 0.1 to 10 g/L.

* * * * *